United States Patent [19]
Zollinger et al.

[11] Patent Number: 5,370,006
[45] Date of Patent: Dec. 6, 1994

[54] PIPING INSPECTION CARRIAGE HAVING AXIALLY DISPLACEABLE SENSOR

[75] Inventors: William T. Zollinger, Martinez; Richard C. Treanor, Augusta, both of Ga.

[73] Assignee: The United States of America as represented by the United States Department of Energy, Washington, D.C.

[21] Appl. No.: 123,248

[22] Filed: Sep. 20, 1993

[51] Int. Cl.$^5$ .................... G01N 29/10; G01N 29/24
[52] U.S. Cl. ................... 73/865.8; 73/623; 324/220
[58] Field of Search ............... 73/865.8, 623, 40.5 P; 324/220, 221; 358/100; 378/60; 104/138.1, 138.2; 105/365

[56] References Cited

U.S. PATENT DOCUMENTS

| | | | |
|---|---|---|---|
| 3,766,775 | 10/1973 | Gunkel | 73/67.8 S |
| 3,926,040 | 12/1975 | Cowell | 73/67.8 S |
| 4,131,018 | 12/1978 | Müller et al. | 73/623 |
| 4,460,920 | 7/1984 | Weber et al. | 358/100 |
| 4,523,468 | 6/1985 | Derkacs et al. | 73/598 |
| 4,581,938 | 4/1986 | Wentzell | 73/623 |
| 4,586,380 | 5/1986 | Patterson | 73/623 |
| 4,856,337 | 8/1989 | Metala et al. | 73/601 |
| 4,864,862 | 9/1989 | Nottingham et al. | 73/623 |
| 5,121,694 | 6/1992 | Zollinger | 104/138.2 |
| 5,189,915 | 3/1993 | Reinhart et al. | 73/623 |
| 5,285,689 | 2/1994 | Hopstack et al. | 73/623 |

FOREIGN PATENT DOCUMENTS

| | | | |
|---|---|---|---|
| 283564 | 11/1990 | Japan | 104/138.2 |
| 2291961 | 12/1990 | Japan | 73/865.8 |
| 1326982 | 7/1987 | U.S.S.R. | 324/220 |

*Primary Examiner*—Hezron E. Williams
*Assistant Examiner*—Daniel S. Larkin
*Attorney, Agent, or Firm*—Brian R. Tumm; Harold H. Dixon; William R. Moser

[57] ABSTRACT

A pipe inspection instrument carriage for use with a pipe crawler for performing internal inspections of piping surfaces. The carriage has a front leg assembly, a rear leg assembly and a central support connecting the two assemblies and for mounting an instrument arm having inspection instruments. The instrument arm has a y-arm mounted distally thereon for axially aligning the inspection instrumentation and a mounting block, a linear actuator and axial movement arm for extending the inspection instruments radially outward to operably position the inspection instruments on the piping interior. Also, the carriage has a rotation motor and gear assembly for rotating the central support and the front leg assembly with respect to the rear leg assembly so that the inspection instruments azimuthally scan the piping interior. The instrument carriage allows performance of all piping inspection operations with a minimum of moving parts, thus decreasing the likelihood of performance failure.

20 Claims, 2 Drawing Sheets

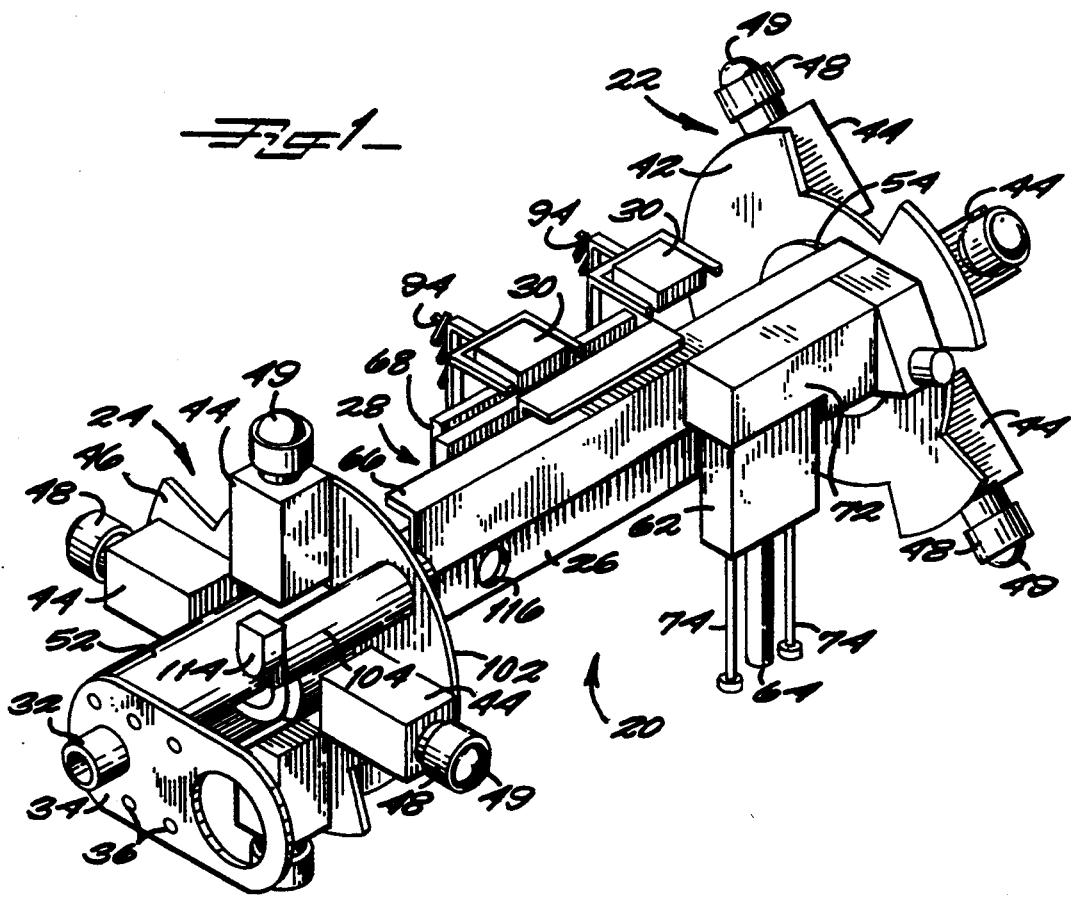
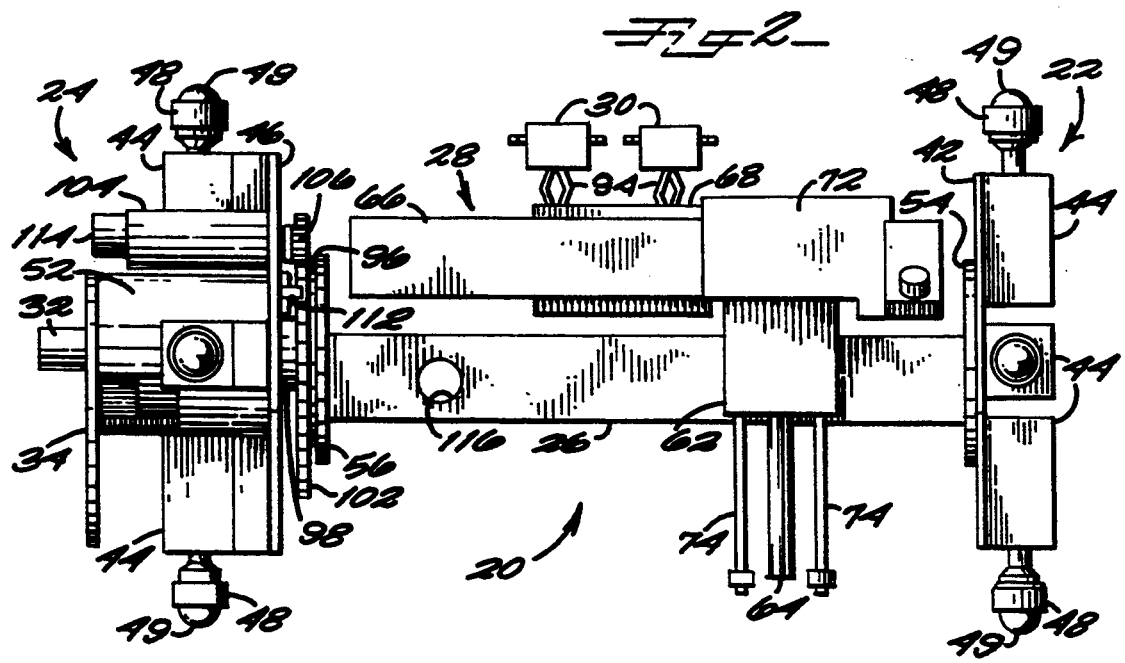

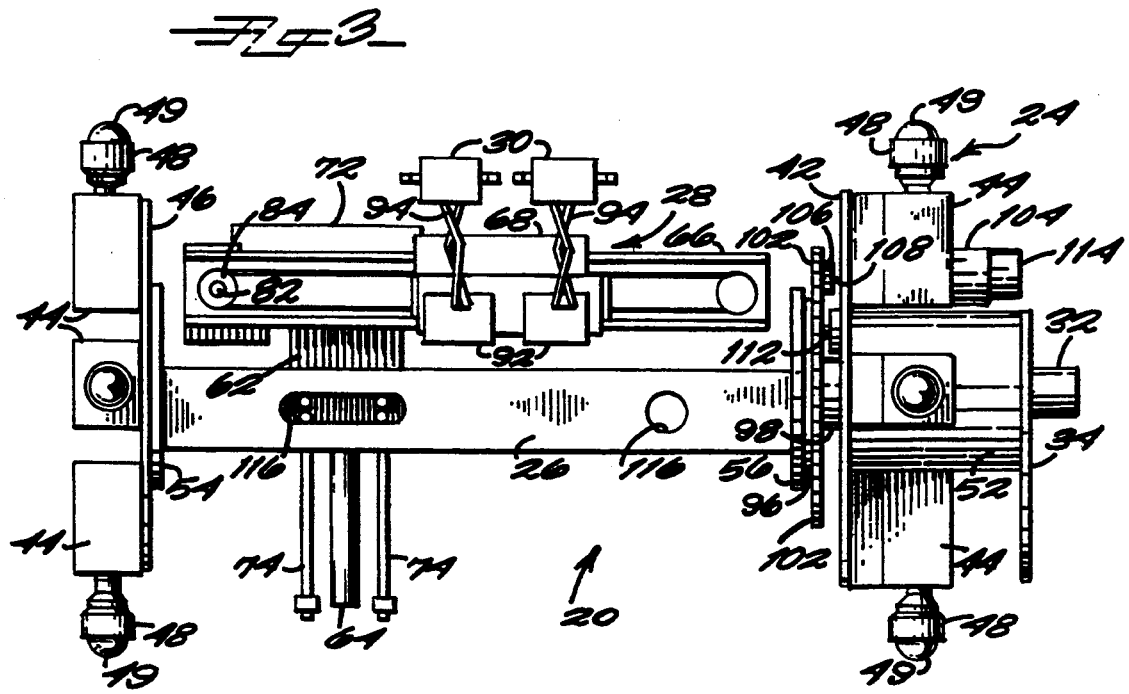
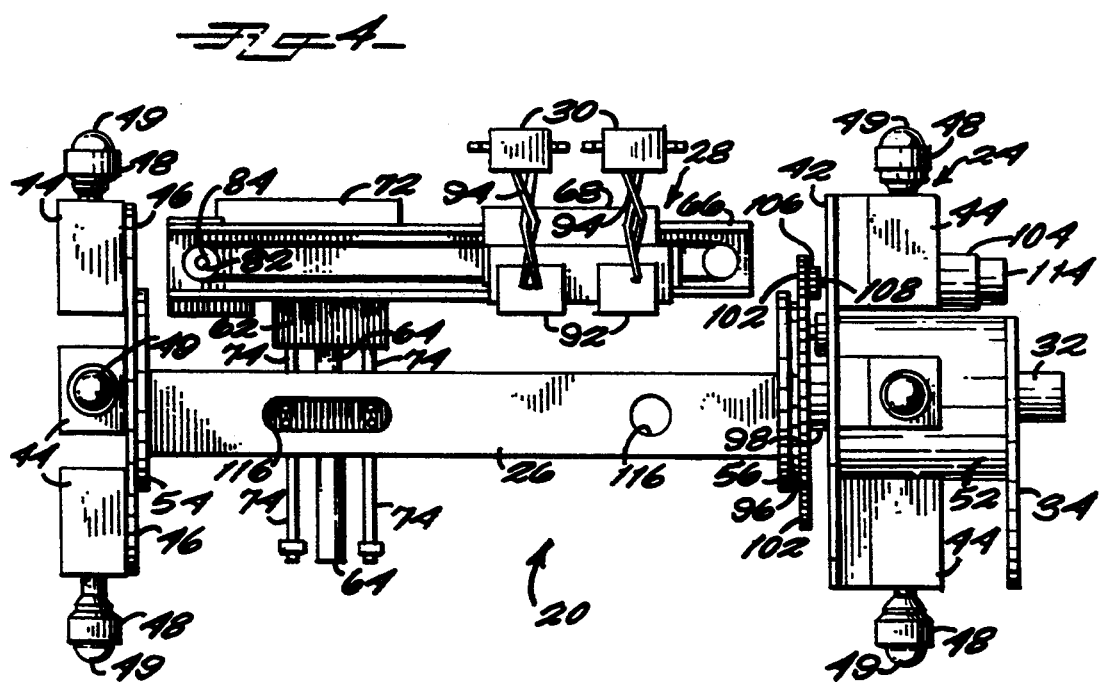

PIPING INSPECTION CARRIAGE HAVING AXIALLY DISPLACEABLE SENSOR

The United States Government has rights in this invention pursuant to Contract No. DE-AC0989SR18035 between the U.S. Department of Energy and Westinghouse Savannah River Company.

BACKGROUND OF THE INVENTION

1. Field of the Invention

The present invention relates to apparatus for inspecting piping. More particularly, the present invention relates to an instrument carriage for use with a pipe crawler to inspect the structural integrity of the interior surface of piping.

2. Discussion of Background

Numerous instrumentation exists for verifying the integrity of piping, including devices for examining their interior and exterior surfaces. Quite often, a scanning device such as an ultrasonic scanner can be used to inspect the exterior surface of piping that is readily accessible.

For piping that is not readily accessible, such as buried piping or piping carrying radioactive or other hazardous materials, devices that inspect the piping's interior surface are often the only means for verifying the integrity of the piping. Some inspection means are self-propelled pipe crawlers having the desired instrumentation mounted thereon. For example, see the pipe crawling devices described by Metal et al in U.S. Pat. No. 4,856,337, Cowell in U.S. Pat. No. 3,926,040 and Weber et al in U.S. Pat. No. 4,460,920.

Other inspection devices consist of carriages transported through the piping by pipe crawlers or other means. A suitable pipe crawler for the present invention and other instrument carriages is described in commonly-assigned U.S. Pat. No. 5,121,694, whose disclosure is incorporated herein by reference. Also, see commonly-assigned U.S. Pat. No. 5,018,451 for a description of another pipe crawler that could be used to move a pipe inspection carriage.

Inspection carriages are well known in the art. Some carriages carry a plurality of inspection equipment, such as ultrasonic probes, eddy current sensors, cameras and the like, but often have limited mobility within the piping once transported therein. Still other carriages carry only selected instruments but offer greater degrees of movement for using the transported equipment.

For example, Nottingham et al, in U.S. Pat. No. 4,864,862, disclose an ultrasonic inspection system featuring a carriage with two radial support assemblies that can move separately to tilt transducers mounted on the carriage.

In U.S. Pat. No. 5,189,915, Reinhart et al disclose an ultrasonic inspection method and apparatus having a carriage that includes a plurality of search units mounted on a housing located between two centering donuts. Each donut contains three dowels spaced 120° apart, for centering the device within the pipe interior. The carriage is also capable of supplying couplant.

Gunkel, in U.S. Pat. No. 3,766,775, discloses a transducer assembly that is rotated within the interior of piping. The device is mounted on a rotable shaft, and the transducer mechanism is stabilized within the pipe by a portable stand. A motor extending from the portable stand controls the movement of the transducer assembly.

Despite the number of carriages that exist, it is desirable to have an instrument-carrying carriage for ultrasonic inspection of piping interior that has greater axial range, yet is still dimensioned to negotiate piping bends.

SUMMARY OF THE INVENTION

The present invention solves the problems associated with the range of axial movement of the inspection instrumentation not addressed by the prior art. According to its major aspects and broadly stated, the present invention is a carriage for pipe inspection equipment. In particular, it is an instrument carriage for use with a pipe crawler or other locomotion means for performing internal inspections of piping surfaces. The carriage has a front leg assembly, a rear leg assembly and a central support therebetween for mounting an instrument arm having inspection instrumentation. The instrument arm has means mounted distally for axially aligning a pair of inspection instruments and means for extending the inspection instruments radially outward to position the inspection instruments on the piping interior. Also, the carriage has means for rotating the central support and the front leg assembly with respect to the rear leg assembly so that the inspection instruments azimuthally scan the piping interior. The instrument carriage allows performance of all piping inspection operations with a minimum of moving parts, thus decreasing the likelihood of performance failure.

A major feature of the present invention is the use of the Y-arm for axial movement of the inspection instruments. The Y-arm is mounted preferably at the distal end of the instrumentation arm, thus axial movement is performed at a location radially displaced from, rather than closer to, the body of the carriage. The advantage of this feature is that the axial movement range of the inspection instruments is increased and more than one inspection instrument can be mounted to the Y-arm for inspection. As a result, much more area can be scanned and much more inspection data can be generated with a minimum of instrument movement once the instrument carriage is positioned.

Another feature of the present invention is the hollow central tube. Besides connecting and maintaining the spacing between the front and rear leg assemblies, the central tube is hollow and dimensioned to house and protect all cabling and wiring necessary for the operation of the instrument carriage and all instruments mounted thereon. This feature significantly reduces the amount of exposed wiring that can snag or restrict movement of the instrument carriage during operation.

Still another feature is the rotation motor and gear assembly. The rotation motor, which is mounted on the rear leg assembly, and the gear assembly, which is rotatably connected to the rear leg assembly, allow the inspection instruments to be moved azimuthally along the piping interior by rotating the central tube and front leg assembly with respect to the rear leg assembly, thereby simplifying the instrumentation motion necessary for inspection. Also, the rotation of the central tube and front leg assembly minimizes the irregular twisting and displacement of the cabling and wiring housed in the central tube and throughout the carriage.

Another feature of the present invention is the linear actuator. The linear actuator is an air-powered assembly that functions to extend the Y-arm and inspection instruments radially outward until the inspection instruments are operably positioned on the interior surface of the piping. This feature contributes to the overall simplification of movement of the inspection instruments during operation, thereby requiring fewer parts and allowing greater freedom of movement and inspection range for the carriage.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a perspective view of an instrument carriage according to a preferred embodiment of the present invention;

FIG. 2 is a detailed view of a first side of the instrument carriage of FIG. 1;

FIG. 3 is a detailed view of a second side of the instrument carriage of FIG. 1; and FIG. 4 is a detailed view of the second side of the instrument carriage showing movement of the extending and axial movement means.

DETAILED DESCRIPTION OF A PREFERRED EMBODIMENT

In the following description similar components are referred to by the same reference numeral in order to simplify the understanding of the sequential aspect of the drawings.

Referring to FIGS. 1-3, the instrument carriage 20 in its preferred embodiment is a front leg assembly 22, a rear leg assembly 24, a central tube 26 for rigidly maintaining the spacing between front leg assembly 22 and rear leg assembly 24, and an instrumentation arm (shown generally as 28) for carrying a plurality of inspection instruments 30 used in inspecting the interior surface of piping or other structures.

Rear leg assembly 24 has a hollow, flexible coupling 32 for connecting instrument carriage 20 to a pipe crawler (not shown). A standard connection arrangement, such as a flange 34 with a plurality of screws 36 (see FIG. 1), is used to fixably mount instrument carriage 20 to the pipe crawler.

The pipe crawler used with instrument carriage 20 can be any type of locomotion means capable of pulling or preferably pushing instrument carriage 20 through piping having a diameter between approximately 12 inches and 16 inches. A suitable pipe crawler for use with instrument carriage 20 is the kind taught in commonly-assigned U.S. Pat. No. 5,121,694, whose disclosure is incorporated herein by reference.

Front leg assembly 22 is a front plate 42, preferably made of aluminum or similar material, having a plurality of radially extendible leg cylinders 44 mounted thereon and spaced equally apart. Similarly, rear leg assembly 24 is a rear plate 46, preferably made of aluminum or similar material, having a plurality of radially extendible leg cylinders 44 mounted thereon and equidistant from one another. The distal end of each leg cylinder has a foot 48, preferably with a ball caster 49, for engaging the interior surface of the pipe being inspected when the leg cylinder is extended radially.

In addition to leg cylinders 44, rear leg assembly 24 has a bearing housing 52 for rotatably connecting central tube 26 to rear leg assembly 24 so that rear leg assembly 24 and central tube 26 are axially aligned with bearing housing 52.

Central tube 26 is preferably a hollow, slender, symmetric housing made of aluminum or similar material. Central tube 26 has a front flange 54 and a rear flange 56 (shown best in FIGS. 2–3), both of which are permanently attached to central tube 26. Front flange 54 is used for fixably attaching central tube 26 to front leg assembly 22 using conventional mounting means such as screws and the like.

Attached to central tube 26 is instrumentation arm 28, which preferably comprises a mounting block 62 having a linear actuator 64, an axial movement arm 66, an instrument support 68 and a motor 72 or other means for moving instrument support 68 along axial movement arm 66.

Mounting block 62 is fixably attached to one side of central tube 26 using any suitable connecting means, such as a plurality of screws or the like. The top of mounting block 62 has a mounting plate (not shown) that is pushed upwards by linear actuator 64, which is preferably an air-powered ram/cylinder combination (as shown in FIG. 4). A pair of actuator stops 74 move with linear actuator 64 to prevent linear actuator 64 from overextending the mounting plate. Because of the mounting location and orientation of mounting block 62, the upward movement of the mounting plate moves instrumentation arm 28 radially outward from central tube 26.

Motor 72 has a housing fixably mounted to the mounting plate by conventional means, such as a plurality of screws or the like. Axial movement arm 66 is mounted to one side of motor 72 so that axial movement arm 66 is oriented as shown in FIGS. 1-3, that is parallel to central tube 26. Motor 72 is oriented within its housing so that a rotating arm 82 (shown in FIG. 3) extends through axial movement arm 66 at one end thereof and has a drive sprocket 84 fixably attached thereto.

Axial movement arm 66 can be any suitable arm that supports inspection instrumentation and provides axial movement thereof, but is preferably the Y-arm from a P-Scan AWS-6 scanner, which is manufactured by P-Scan and is part of their external pipe inspection kit. Also, motor 72 is preferably the motor as part of the P-Scan external pipe inspection kit, but with a modified housing.

Compared to previous pipe crawler instrumentation carriages, the Y-arm from a P-Scan AWS-6 scanner is configured for using multiple probes and is very compact for the amount of linear or axial travel it provides. Also, the Y-arm, as is, is suitable for keeping a proper orientation of the probes with the interior surface of a pipe wall with sufficient compliance. Moreover, the Y-arm can supply couplant directly to the probes.

Drive sprocket 84 is used in operable connection with an endless belt 86 and a driven sprocket 88 to slide instrument support 68 axially along axial movement arm 66 (as shown in FIG. 4). Preferably, axial movement arm is approximately 11" long, thus, taking into consideration the size of instrument support 68, inspection instruments 30 are afforded axial movement of approximately 8" in this configuration.

Instrument support 68 is dimensioned to mount at least one and preferably two inspection instruments 30 such as ultrasonic probes, eddy current probes and the like. Inspection instruments 30 are commercially available and spring mounted on clamps 92 using a plurality of linkages 94, or alternatively, coiled springs (not shown). In the preferred embodiment, linkages 94 that offer a vertical "play" of approximately 2" are used.

Using clamps 92, inspection instruments 30 are connected to instrument support 68.

Preferably, inspection instruments 30 are a pair of ultrasonic probes, which are used to determine the distance to a wave-reflecting internal crack or other flaw in the interior of piping. In use, the ultrasonic probes direct ultrasonic signals into the interior surface of piping of other structures using the signal generator portion of the probes. Flaws in the piping represent acoustic discontinuities that reflect back a portion of the signal energy to the signal receiver portion of the probes. For convenience, some ultrasonic probes are equipped to function as both signal generator and receiver.

In the present invention, when the ultrasonic probes are used as inspection instruments 30, each probe preferably functions as both the signal generator and receiver. Thus, preferably, the first probe is oriented on instrument support 68 to produce 45° shear waves to look for and measure intergranual stress corrosion cracking (SCC) and the second probe is oriented on instrument support 68 to produce 90° "straight-through" waves for measuring wall thickness of the piping being inspected. Both measurements are needed in the normal inspection process.

Alternatively, eddy current probes can be used as inspection instruments 30. Eddy current probes test magnetic properties and look for a change in those properties present due to welding or other instigators.

Rear flange 56 of central tube 26 is fixably attached to a rotating means having a flanged portion 96 and a nosepiece 98 that inserts into and rotates within bearing housing 52. Preferably, a large annular rotation gear 102 is coupled between the rotating means and rear leg assembly 24 so that when rear flange 56 of central tube 26 is fixably attached to flanged portion 96, rotation gear 102 rotates both central tube 26 and front leg assembly 22 with respect to rear leg assembly 24.

Rotation gear 102 is driven by use of a rotation motor 104 fixably mounted on rear leg assembly 24. Rotation motor 104 has a rotation pinion 106 mounted on a sprocket 108 that passes through an aperture (not shown) formed in rear leg assembly 24. Rotation motor 104 can be any commercially available motor having the requisite specifications for proper operation of rotation gear 102.

In order to rotate central tube 26 with respect to rear leg assembly 24, rotation motor 104 is operated to rotate sprocket 108, which rotates rotation pinion 106, in the desired direction. Rotation pinion 106 has a plurality of teeth that mesh with a corresponding plurality of teeth along the peripheral edge of annular rotation gear 102 so that annular rotation gear 102 rotates when rotation pinion 106 is rotated.

Annular rotation gear 102 has a raised head (not shown) mounted thereon that aligns with a mechanical stop 112 (see FIG. 2) mounted on rear leg assembly 24. Mechanical stop 112 is positioned on rear leg assembly 24 so that it comes into contact with the raised head once annular rotation gear 102 has been rotated just beyond 360° (approximately 365°).

Preferably, rotation motor 104 comes equipped with a built-in encoder 114 or similar means for tracking precisely the rate of incremental rotation and the rate at which rotation motor 104 rotates annular rotation gear 102, and consequently central tube 26 and front leg assembly 22. Such rotational monitoring is important and necessary in processing inspection data. Also, industry standards for scanning surfaces such as piping interiors must be adhered to and require a certain degree of accuracy with respect to rotational monitoring.

Central tube 26 is preferably dimensioned to house and allow passage of all wiring and tubing of instrumentation carriage 20. Thus, central tube 26 effectively eliminates almost all exposed cabling that could otherwise snag within the piping or restrict movement as central tube 26 rotates. Preferably, wiring enters instrument carriage 20 from the pipe crawler through coupling 32 and passes through the center of bearing housing 52 and rear leg assembly 24 to central tube 26. Also, a plurality of ports 116 are formed in central tube 26 so that the wiring can access appropriate equipment at appropriate places along central tube 26.

Preferably, carriage 20 has a plurality of cameras (not shown) mounted thereto to provide aid in positioning carriage 20 in the desired location within the piping. Cameras can be mounted on front leg assembly 22, rear leg assembly 24, and central tube 26. Also, cameras are mounted on central tube 26 midway between front and rear leg assemblies 22, 24 for viewing various portions of the piping region to be inspected.

Instrument carriage 20 is controlled through an umbilical cable running from the rear of instrument carriage 20 back through the pipe crawler and the interior of the piping to a control cabinet. The umbilical cable routes control signals for air valves, air for leg cylinders 44, data signals from inspection instruments 30, and electrical power for motor operation. Alternatively, the valve for supplying air to leg cylinders 44 can be conveniently located on the pipe crawler or back at the controls.

In use, instrument carriage 20 is used with a pipe crawler for inspecting the interior surface of piping having a diameter approximately 12 inches to approximately 16 inches. Initially, all leg cylinders 44 are retracted and rear leg assembly 24 connects instrument carriage 20 to the front of the pipe crawler via flexible coupling 32 and all necessary wiring is run from the pipe crawler to instrument carriage 20 for proper operation.

Once entering the piping, instrument carriage 20 is preferably pushed through the piping interior to the desired position using locomotion provided by the pipe crawler and the viewing assistance of the mounted cameras. Ball casters 49 provide instrument carriage 20 with the directional smoothness to roll axially down the piping interior. Flexible coupling 32 allows the pipe crawler and carriage 20 combination to negotiate elbows in the piping. Preferably, instrument carriage 20 is eventually positioned so that an area to be inspected is approximately midway between front and rear leg assemblies 22, 24.

Once in the desired position within the piping, leg cylinders 44 are radially extended until casters 49 engage the interior surface of the piping so that instrument carriage 20 remains centered in the piping. Then, linear actuator 64 radially extends instrumentation arm 28 until inspection instruments 30 are operably positioned along the interior surface of the piping. Instrument support 68 can be slid axially in either direction, in the manner discussed above, to position the inspection instruments 30 preferably on either side of the weld being inspected. When inspecting welds, the desired inspection region is preferably within 3" on either side of the weld, which is the most crucial area to be scanned for defects. Since inspection instruments 30 are preferably clamped on instrument support 68, the distance between inspection instruments 30 can be increased or decreased as necessary depending on the type of feature being inspected.

Next, using rotation motor 104 as discussed above, central tube 26 and front leg assembly 22 are rotated incrementally so that inspection instruments 30 travel azimuthally along the interior of the piping. Once again, ball casters 49 provide instrument carriage 20 with the directional smoothness to roll azimuthally. During this movement, the pipe crawler preferably has a firm grip within the interior of the piping, thus allowing such rotation to occur without difficulty. In the present invention, the preferred use of two inspection instruments 30 eliminates the need for a single inspection instrument being rotated at each inspection site. That is, previous single probe carriages moved the inspection probe in a systematic square wave path along weld.

Once inspection instruments 30 have scanned the entire circumference of the piping interior, that is, central tube 26 has rotated just over 360° (approximately 365°), the head mounted on rear plate 46 will hit stop 112, and operational controls will reverse the direction of rotation to "unwind" central tube 26 and inspection instruments 30 to their original azimuthal position. Then, linear actuator 64 will retract inspection instruments 30 and carriage 20 will be repositioned axially along the piping interior for the next scan.

It will be apparent to those skilled in the art that many changes and substitutions can be made to the preferred embodiment herein described without departing from the spirit and scope of the present invention as defined by the appended claims.

What is claimed is:

1. Apparatus for inspecting a feature on the interior surface of piping, said apparatus comprising:
   a front leg assembly having a first plurality of radially extendible legs for centering and supporting said front leg assembly within said piping;
   a rear leg assembly spaced apart from said first leg assembly, said rear leg assembly having a second plurality of radially extendible legs for centering and supporting said rear leg assembly within said piping;
   means for connecting said front and rear leg assemblies, said connecting means having an axis of rotation;
   at least one inspection instrument adapted for scanning said feature and producing an output having information about said feature;
   an instrumentation arm having a proximal end attached to said connecting means and a distal end; and
   means carried by said distal end of said instrumentation arm for axial moving said inspection instrument with respect to said connecting means, said instrumentation arm extending said axial moving means radially outward from said connecting means so that said inspection instrument is operably positioned along said interior surface of said piping.

2. The apparatus as recited in claim 1, wherein said axially moving means further comprises:
   an axial movement arm mounted to said distal end of said instrumentation arm;
   an instrumentation support carrying said inspection instrument and slidably positioned on said axial movement arm for sliding said inspection instrument in a direction parallel to said axis of rotation; and
   motorized means mounted to said instrumentation support and oriented to slidably move said inspection instrument along said support.

3. The apparatus as recited in claim 1, further comprising means in operable connection with said connecting means for rotating said connecting means about said axis of rotation so that, when said inspection instrument is positioned along said interior surface of said piping, said inspection instrument is rotated azimuthally along said interior of said piping to scan said feature.

4. The apparatus as recited in claim 1, wherein said instrumentation arm further comprises an actuator for extending said distal end of said instrumentation arm radially outward from said connecting means so that said inspection instrument is positioned operably along said interior surface of said piping.

5. The apparatus as recited in claim 1, wherein said connecting means has a first end fixably attached to said front leg assembly and a second end rotatably attached to said rear leg assembly, and wherein said apparatus further comprises means for rotating said connecting means about said axis of rotation, said rotating means having:
   a rotation gear carried by said second end of said connecting means for rotatably connecting said connecting means to said rear leg assembly, said rotation gear rotating said connecting means about said axis of rotation and with respect to said rear leg assembly; and
   a rotation motor mounted to said rear leg assembly, said rotation motor having a rotation pinion in operable connection with said rotation gear, said rotation pinion rotating said rotation gear when rotated by said rotation motor.

6. The apparatus as recited in claim 1, wherein each extendible leg of said first and second plurality of radially extendible legs has an air cylinder mounted therein for radially extending said each extendible leg in response to air being supplied to said each air cylinder.

7. The apparatus as recited in claim 1, wherein each of said front leg assembly, said connecting means and said rear leg assembly has means formed therein for housing wiring and cables used in operating said radially extendible legs, said inspection instrument, said axially moving means and said rotating means.

8. The apparatus as recited in claim 1, wherein said apparatus is for use with a pipe crawler, wherein said apparatus further comprises means carried by said rear leg assembly for coupling said apparatus to said pipe crawler, said coupling means being flexible and having means formed therein for housing wiring and cables used in operating said radially extendible legs, said inspection instrument, said axially moving means and said rotating means.

9. Apparatus for inspecting a feature on the interior surface of piping, said apparatus for use with a pipe crawler, said apparatus comprising:
   a frame having a first end, a second end and an axis of rotation;
   a front leg assembly fixably attached to said first end of said frame;
   a rear leg assembly rotatably attached to said second end of said frame,
   each of said front and rear leg assemblies having means for centering and supporting said apparatus within said piping;

at least one inspection instrument adapted for scanning said feature and producing an output having information about said feature;

an instrumentation arm having a proximal end and a distal end, said proximal end attached to said frame;

means carried by said distal end of said instrumentation arm for axially moving said inspection instrument with respect to said frame, said instrumentation arm slidably mounted on said axially moving means; and means for rotating said frame and said front leg assembly about said axis of rotation so that, when said inspection instrument is positioned along said interior surface of said piping, said inspection instrument is rotated azimuthally along said interior of said piping.

10. The apparatus as recited in claim 9, wherein said axially moving means further comprises:

an axial movement arm carried by said distal end of said instrumentation arm;

a motor mounted on said axial movement arm;

a belt carried by said axial movement arm and in operable connection with said motor; and an instrumentation support carrying said inspection instrument, said instrumentation support attached to said conveyor so that when said motor rotates to operate said belt, said instrumentation support slides along said axial movement arm in a direction parallel to said axis of rotation.

11. The apparatus as recited in claim 9, wherein said instrumentation arm further comprises a linear actuator, said linear actuator having an air cylinder for extending said distal end of said instrumentation arm radially outward from said frame so that said inspection instrument is operably positioned along said interior surface of said piping.

12. The apparatus as recited in claim 9, wherein said rotating means further comprises:

a rotation gear fixably attached to said second end of said frame:

a bearing assembly carried by said rear leg assembly for rotatably connecting said second end of said frame to said rear leg assembly, said rotation gear oriented for rotating said frame and said front leg assembly about said axis of rotation and with respect to said rear leg assembly; and a rotation motor mounted to said rear leg assembly, said rotation motor having a rotation pinion positioned in operable connection with said rotation gear to rotate said rotation gear when said motor rotates said rotation pinion.

13. The apparatus as recited in claim 9, wherein said inspection instrument further comprises:

a first inspection probe mounted to said axially moving means and oriented with respect to said interior surface of said piping to generate a shear wave when operably positioned along said interior surface of said piping; and a second inspection probe mounted to said axially moving means and oriented with respect to said interior surface of said piping to generate a straight-through wave when operably positioned along said interior surface of said piping.

14. The apparatus as recited in claim 9, wherein said centering means further comprises:

a first plurality of radially extendible legs attached to said first assembly; and a second plurality of radially extendible legs attached to said second assembly, each leg of said first and second plurality of radially extendible legs having a proximal end, a distal end and an air cylinder mounted therein for radially extending said radially extendible leg in response to air being when supplied to said each air cylinder, each of said distal ends having a ball caster for allowing movement of said apparatus within said piping.

15. The apparatus as recited in claim 9, wherein said inspection instrument further comprises a pair of inspection probes selected from the group consisting of an ultrasonic probe and an eddy current probe.

16. The apparatus as recited in claim 9, wherein each of said front leg assembly, said frame, said rear leg assembly and said rotating means has means formed therein for housing wiring and cables used in operating said front and rear leg assemblies, said inspection instrument, said axially moving means and said rotating means.

17. The apparatus as recited in claim 9, further comprising a flexible coupler carried by said rear leg assembly for coupling said apparatus to said pipe crawler so that pipe crawler moves said apparatus through said piping, said coupling means having means formed therein for housing wiring and cables used in operating said front and rear leg assemblies, said inspection instrument, said axially moving means and said rotating means.

18. An instrument carriage for inspecting a feature on the interior surface of piping, said carriage for use with a pipe crawler, said carriage comprising:

a central tube having a first end, a second end and an axis of rotation;

a front assembly fixably attached to said first end of said central tube, said front assembly having a first plurality of radially extendible legs mounted thereto;

a rear assembly rotatably attached to said second end of said central tube, said rear assembly having a second plurality of radially extendible legs mounted thereto, each leg of said first and second plurality of radially extendible legs having a proximal end, a distal end and an air cylinder mounted therein for extending said radially extendible leg whereby said apparatus is centered and supported within said piping;

a pair of inspection probes adapted for scanning said feature and producing an output having information about said feature;

an instrumentation arm having a proximal end attached to said central tube and a distal end;

means carried by said distal end of said instrumentation arm for axially moving said inspection probes with respect to said central tube, said instrumentation arm extending said axially moving means radially outward from said connecting means so that said inspection probes are positioned along said interior surface of said piping; and means for rotating said central tube and said front assembly about said axis of rotation and with respect to said rear assembly so that, when said inspection probes are positioned along said interior surface of said piping said inspection probes travel azimuthally along said interior surface of said piping to scan said feature, said rotating means having a rotation gear fixably attached to said second end of said central tube;

a bearing assembly carried by said rear leg assembly for rotatably connecting said second end of said central tube to said rear assembly, said rotation gear oriented for rotating said central tube and said front assembly about said axis of rotation and with respect to said rear assembly, and a rotation motor mounted to said rear assembly, said rotation motor having a rotation pinion positioned in operable connection with said rotation gear to rotate said rotation gear when said rotation motor rotates said rotation pinion.

19. The instrumentation carriage as recited in claim 18, wherein said axially moving means further comprises:

an axial movement arm carried by said distal end of said instrumentation arm;

a motor mounted on said axial movement arm;

a belt carried by said axial movement arm and in operable connection with said motor; and an instrumentation support carrying said inspection probes, said instrumentation support attached to said conveyor so that when said motor rotates to operate said belt, said instrumentation support slides along said axial movement arm in a direction parallel to said axis of rotation.

20. The instrumentation carriage as recited in claim 18, wherein said inspection probes further comprise:

a first inspection probe spring mounted to said axially moving means and oriented with respect to said interior surface of said piping to generate a shear wave when operably positioned along said interior surface of said piping; and a second inspection probe spring mounted to said axially moving means and oriented with respect to said interior surface of said piping to generate a straight-through wave when operably positioned along said interior surface of said piping.

* * * * *